United States Patent [19]

Barnish et al.

[11] 4,219,566

[45] Aug. 26, 1980

[54] PHENYLGLYOXYLIC ACIDS AND DERIVATIVES THEREOF

[75] Inventors: Ian T. Barnish, Ramsgate; Peter E. Cross, Canterbury; John C. Danilewicz, Ash, N. Canterbury; Malcolm Morville, Margate, all of England; Michael G. Page, Waterford, Conn.

[73] Assignee: Pfizer Inc., New York, N.Y.

[21] Appl. No.: 915,904

[22] Filed: Jun. 16, 1978

[30] Foreign Application Priority Data

Jul. 1, 1977 [GB] United Kingdom ............... 27756/77

[51] Int. Cl.² .................. A61K 31/19; A61K 31/235; A61K 31/22
[52] U.S. Cl. .................................... 424/317; 424/308; 424/311
[58] Field of Search ............................... 424/317, 308

[56] References Cited

U.S. PATENT DOCUMENTS

| | | | |
|---|---|---|---|
| 3,532,737 | 10/1970 | Siggins | 260/476 |
| 3,657,325 | 4/1972 | Siggins | 260/483 |
| 3,754,006 | 8/1973 | Siggins | 260/332.2 A |
| 3,830,930 | 8/1974 | Moeller et al. | 424/308 |

FOREIGN PATENT DOCUMENTS 949521 9/1956 Fed. Rep. of Germany ........... 424/317

OTHER PUBLICATIONS

*Chem. Abstr.*, vol. 52, p. 19024.

*Primary Examiner*—Frederick E. Waddell
*Attorney, Agent, or Firm*—Connolly and Hutz

[57] ABSTRACT

The use of phenylglyoxylic acids and derivatives thereof in the treatment of ischemic heart disease and the hyperglycemia of diabetes.

3 Claims, No Drawings

PHENYLGLYOXYLIC ACIDS AND DERIVATIVES THEREOF

BACKGROUND OF THE INVENTION

1. Field of the Invention

The invention relates to the novel use of certain phenylglyoxylic acids and derivatives thereof in the treatment of ischemic heart disease and the hyperglycemia of diabetes. The invention also relates to a pharmaceutical composition of the useful compounds in a unit dosage form.

2. Description of the Prior Art

Ischemic heart disease is characterized by the obstruction of the major blood vessels which service the heart, resulting in decreased oxygen supply to myocardial tissue. During physical stress the reduction in the myocardial oxygen supply results in extreme cardiac pain known as angina pectoris.

Although nitrates, such as nitroglycerin, are the drugs of choice as vasodilators in the treatment of ischemic heart disease, they suffer from a short duration of action.

Diabetes, which is characterized by the elevation of blood-glucose levels, is most frequently treated today by diet, insulin injections or sulfonylurea therapy. Dieting as a means of controlling the symptoms of this disease is sometimes quite difficult and is not sufficient in cases where the diabetes is severe; insulin injections are especially useful in advanced stages of this disease or where the patient does not have an effectively functioning pancreas; and sulfonylureas are useful in the more moderately severe cases of diabetes where the patient does have a functioning pancreas.

The compounds which are the subject of this use invention are effective in the treatment of ischemic heart disease and in combatting the hyperglycemia of diabetes.

The compounds of the present invention and various derivatives thereof are known in the art. German Pat. No. 949,521 discloses a substantial number of phenylglyoxylic acids as sun screening agents.

U.S. Pat. Nos. 3,532,737; 3,657,325 and 3,754,006 claim a variety of substituted alkyl esters of phenylglyoxylic acid as hypoglycemic agents useful in lowering the blood sugar levels in diabetic subjects.

SUMMARY OF THE INVENTION

A method has now been found for treating ischemic heart disease in a human subject suffering from that disease which comprises orally or parenterally administering to said subject an ischemic heart disease treating amount of a compound selected from the group consisting of those of the formula

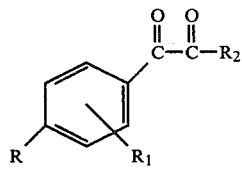

wherein R is hydrogen, alkyl having one to four carbon atoms, hydroxy, alkoxy having one to four carbon atoms, alkylthio having one to five carbon atoms, alkanoyloxy having two to four carbon atoms, chloro, bromo, fluoro or iodo; $R_1$ is hydrogen, alkyl having one to four carbon atoms, chloro, bromo, fluoro or iodo; $R_2$ is hydroxy or alkoxy having one to four carbon atoms; and a pharmaceutically acceptable base salt wherein $R_2$ is hydroxy.

A preferred group of compounds for this method of treating ischemic heart disease are those of formula I wherein $R_1$ is hydrogen and $R_2$ is hydroxy. Especially preferred within said group are p-hydroxyphenylglyoxylic acid, p-methoxyphenylglyoxylic acid, p-methylthiophenylglyoxylic acid, p-ethylthiophenylglyoxylic acid, p-methylphenylglyoxylic acid, and p-chlorophenylglyoxylic acid and their pharmaceutically acceptable base salts.

In addition, a method has been found for treating diabetes in a human subject which comprises orally or parenterally administering to said subject a diabetes treating amount of a compound selected from the group consisting of those of the formula

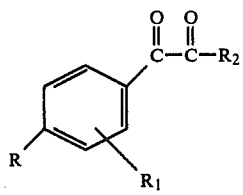

wherein R is hydrogen, alkyl having one to four carbon atoms, hydroxy, alkoxy having one to four carbon atoms, alkylthio having one to five carbon atoms, alkanoyloxy having two to four carbon atoms, chloro, bromo, fluoro or iodo; $R_1$ is hydrogen, alkyl having one to four carbon atoms, chloro, bromo, fluoro or iodo; $R_2$ is hydroxy or alkoxy having one to four carbon atoms; and a pharmaceutically acceptable base salt wherein $R_2$ is hydroxy.

A preferred group of compounds for this method of treating the hyperglycemia of diabetes are those of formula I wherein $R_1$ is hydrogen and $R_2$ is hydroxy. Especially preferred with this group is p-hydroxyphenylglyoxylic acid and its pharmaceutically acceptable base salts.

The invention further provides for a composition of matter in unit dosage form suitable for treating ischemic heart disease or diabetes which comprises a pharmaceutically acceptable carrier and from about 70-750 mg. of an active compound of the formula I or a pharmaceutically acceptable base salt thereof.

DETAILED DESCRIPTION OF THE INVENTION

As previously mentioned, the compounds of the present method invention are either known in the art or can readily be prepared by methods reported in the chemical literature.

In addition to the free acids, the present invention is also meant to embrace their pharmaceutically acceptable base salts and simple alkyl esters.

The phenylglyoxylic acids are converted to their basic salts by the interaction of said acids with an appropriate base in an aqueous or non-aqueous medium. Such basic reagents suitably employed in the preparation of said salts can vary in nature, and are meant to contemplate such bases as organic amines, ammonia, amino acids, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, tertiary amines such as diethylaniline, N-methylpyrrolidine, N-methylmorpholine and 1,5-diazabicyclo[4,3,0]-5-nonene; sodium hydroxide, potassium hydroxide, ammonium hydroxide, sodium ethoxide, potassium methoxide, magnesium hydroxide, calcium hydride and barium hydroxide. The preferred basic salts are sodium, potassium, calcium, ammonium and the salts with meglumine, ethanolamine and choline.

The compounds of the formula (I) may be administered to patients in admixture with or dissolved in a pharmaceutically-acceptable carrier selected with regard to the intended route of administration and standard pharmaceutical practice.

For example, they may be administered orally in the form of tablets or capsules containing a unit dose of the compound of the formula (I) together with such excipients as maize starch, calcium carbonate, dicalcium phosphate, alginic acid, lactose, magnesium stearate, "Primogel" (Trade Mark) or talc. The tablets are typically prepared by granulating the ingredients together and compressing the resulting mixture to tablets of the desired size. The capsules are typically prepared by granulating the ingredients together and filling them into hard gelatin capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes, for example enough salts (e.g. sodium acetate, sodium lactate, sodium citrate, sodium succinate or sodium chloride or dextrose (e.g. 5% anhydrous dextrose injection BP) to make the solution isotonic. A pharmaceutically-acceptable organic solvent such as polyethylene glycol or ethanol may also replace part of the water. An antioxidant such as sodium metabisulphite may also be present, typically in an amount of up to 0.1% by weight. Such parenteral formulations may be prepared by conventional methods. For example, in a typical procedure involving the preparation of a succinate-containing intravenous formulation, a 0.2 molar solution of succinic acid may be mixed with a 0.2 molar solution of sodium hydroxide to give a solution of pH 5. The compound of the formula (I) is then typically dissolved in the succinate solution in an amount of 1-2% on a weight/volume basis. The resulting solution may then be sterilized according to the method of B.P. 1973 by filtration through a bacteria-proof filter under aseptic conditions into sterile containers so as to comply with the test for sterility of Appendix 121, B.P. 1973. Suitable containers are for example sterile glass vials of an appropriate size to contain the desired volume of solution, which volume will typically contain a unit dose of the compound of the formula (I). The compounds of the formula (I) may also be administered by the infusion of a parenteral formulation as described above into a vein.

For oral administration to human patients with ischemic heart disease or who have diabetes, the daily dosage level of a compound of the formula (I) is from 5 to 70 mg./kg., preferably 20-50 mg./kg., per day for a typical adult patient (70 kg.). For parenteral administration, the daily dosage level of a compound of the formula (I) is from 1-10 mg./kg., preferably 2-5 mg./kg. per day, for a typical adult patient. Thus tablets or capsules can generally be expected to contain from 150 mg. to 1 g. of the active compound for administration orally up to 5 times a day. Dosage units for parenteral administration can be expected to contain from 70-750 mg. of the active compound. A typical vial could be a 50 ml. vial containing 70-750 mg. of the active compound in 30-50 ml. of solution.

It should of course be appreciated that the physician in any event will determine the actual dosage which will be most suitable for the individual and it will vary with the age, weight and response of the patient. The above dosages are exemplary of the average host. There may of course be individual cases where higher or lower dosage ranges are merited.

The activity of the compounds of the formula (I) in treating ischemic heart disease is assessed by their abilities to:

(1) increase the oxidation of glucose and/or pyruvate by isolated rat muscle preparation in vitro;

(2) increase the proportion of the active form of the enzyme pyruvate dehydrogenase (PDH) in organs of animals (e.g. rats) in vivo; and (3) reduce oxygen demand and affect the relative utilization of carbohydrate and lipid metabolites by the electrically-paced heart of an anesthetized dog in the presence or absence of an isoprenaline stimulus.

The activity of the compounds of formula (I) in treating diabetics is assessed by their abilities to:

(4) decrease blood glucose levels in animals made diabetic by chemical lesion of the pancreas.

Activity in tests for (1) is indicative of the potential utility of the compounds in the treatment of ischemic heart disease, cardiac failure, cerebral insufficiency, maturity-onset diabetes or obesity.

Activity in tests for (2) is further indicative of their potential utility in the treatment of these diseases or conditions and, in particular, activity in an animal heart in vivo is indicative of utility in the treatment of ischemic heart disease and cardiac failure.

Activity in tests for (3) is further indicative of thier potential utility in the treatment or ischemic heart disease and cardiac failure. Activity in tests for (4) is indicative of their potential utility in the treatment of diabetes.

The invention is illustrated by the following Examples.

EXAMPLE 1

Glacial acetic acid (12.0 gm.) was dissolved in freshly distilled water to produce 1000 ml. of a 0.2 molar solution.

Sodium acetate anhydrous (16.4 gm.) was dissolved in freshly distilled water to produce 1000 ml. of a 0.2 molar solution.

148.0 ml. of the acetic acid solution (0.2 molar) was then mixed with 352.0 ml. of the sodium acetate solution (0.2 molar), the mixture being made up to 1000 ml. with freshly distilled water. The resulting solution had a pH of 5, and 10.0 gm. (0.056 moles) of p-hydroxyphenylglyoxylic acid was then added to it.

This final solution was then sterilized according to the method of the B.P. 1973 by filtration through a suitable bacteria-proof filter under aseptic conditions into sterile containers so as to comply with the test for sterility of Appendix 121, B.P. 1973. Suitable containers are sterile 50 ml. glass vials, which are filled with 30 ml. of the final solution, i.e. the resulting vials contain 300 mg. of the active ingredient.

EXAMPLE 2

Succinic acid (23.62 gm.) was dissolved in freshly distilled water to produce 1000 ml. of a 0.2 molar solution. Sodium hydroxide (8 g.) was dissolved in freshly distilled water to produce 1000 ml. of a 0.2 molar solution.

250 ml. of the 0.2 molar succinic acid solution was then mixed with 267.0 ml. of the 0.2 molar sodium hydroxide solution, the mixture being made up to 1000 ml. with freshly distilled water. 10.0 g. (0.056 moles) of p-hydroxyphenylglyoxylic acid was dissolved in the resulting solution. The resulting solution was sterilized according to the method of B.P. 1973 by filtration through a bacteria-proof filter under aseptic conditions into sterile containers to comply with the test for sterility of the B.P. 1973 (Appendix 121). Suitable containers are sterile glass vials, which are filled with 40 ml. of the final solution. The resulting vials therefore contain 400 mg. of the active ingredient.

EXAMPLE 3

Citric acid monohydrate (21.0 gm.) was dissolved in 200.0 ml. of 0.1 M NaOH (4 gm./l.), and the resulting solution was made up to 1000 ml. with freshly distilled and cooled water. 963.0 ml. of this solution was then made up to 1000 ml. with 0.1 M HCl, and p-hydroxyphenylglyoxylic acid (10.0 gm., 0.056 moles) was then added.

This final solution was then sterilized according to the method of the B.P. 1973 by filtration through a bacteria-proof filter of suitable composition under aseptic conditions into sterile containers, so as to comply with the test for sterility of Appendix 121, B.P. 1973. Suitable containers are sterile 50 ml. glass vials, which are filled with 50 ml. of the final solution, the resulting vials containing 500 mg. of the active ingredient.

EXAMPLE 4

Oxygen-free water for injection was prepared by purging freshly distilled water with nitrogen for 30 minutes. Throughout the following operations a nitrogen blanket was maintained over the exposed solution. Sodium chloride (200 mg.) and p-hydroxyphenylglyoxylic acid (750 mg.) were then dispersed with stirring in 20 ml. of the thus-prepared water for injection. Dilute sodium hydroxide solution (1.0 N, 4.0 ml.) was then added. The pH of the solution was then adjusted to pH 7.0±0.2 by the addition of 0.1 N sodium hydroxide solution, and the solution then made up to 50 ml. with the said water for injection. This final solution was then sterilized according to the method of the B.P. 1973 by filtration through a suitable bacteria-proof filter under aseptic conditions into sterile containers, so as to comply with the test for sterility of Appendix 121, B.P. 1973. Suitable containers are sterile 50 ml. glass vials, which are filled with 50 ml. of solution, the resulting vials containing 750 mg. of the active ingredient.

EXAMPLES 5 TO 7

Vials containing 50 ml. of the following formulations were prepared similarly to Example 4, except that in Examples 6 and 7, sodium metabisulphite (5.0 ml. of a 3.0 mg./ml. solution) was added after addition of the 0.1 N caustic soda.

| Example No. | Formulation | |
|---|---|---|
| 5 | p-hydroxyphenylglyoxylic acid | 750 mg. |
| | sodium chloride | 200 mg. |
| | dilute sodium hydroxide solution | sufficient to produce a pH of 5.0 ± 0.2 |
| | water for injection | balance to 50 ml. |
| 6 | p-hydroxyphenylglyoxylic acid | 750 mg. |
| | sodium chloride | 200 mg. |
| | sodium metabisulfite | 15 mg. |
| | dilute sodium hydroxide solution | sufficient to produce a pH of 7.0 ± 0.2 |
| | water for injection | balance to 50 ml. |
| 7 | p-hydroxyphenylglyoxylic acid | 750 mg. |
| | sodium chloride | 200 mg. |
| | sodium metabisulphite | 15 mg. |
| | dilute sodium hydroxide solution | sufficient to produce a pH of 5.0 ± 0.2 |
| | water for injection | balance to 50 ml. |

EXAMPLE 8

Oxygen-free water for injection was prepared by purging freshly distilled water with nitrogen for 30 minutes. A nitrogen blanket was maintained over the solution throughout the following operations. L-Aspartic acid (500 mg.) and sodium chloride (150 mg.) were then dispersed with stirring in 30 ml. of the thus-prepared water for injection. Dilute (1.0 N) sodium hydroxide solution was then added until the pH was 4.5±0.1. p-Hydroxyphenylglyoxylic acid (750 mg.) was then added with stirring, and the resulting solution was then made up to 50 ml. with the said water for injection.

The solution was sterilized and put into a 50 ml. vial as described in Example 4.

EXAMPLE 9

The procedure of Example 8 was repeated with the addition of 5.0 ml. of a 3.0 mg./ml. solution of sodium metabisulphite immediately after the addition of the glyoxylic acid.

EXAMPLE 10

Formulations containing phenylglyoxylic acid, ethyl p-hydroxyphenylglyoxylate, p-hydroxy-m-methylphenylglyoxylic acid, p-hydroxy-m-iodophenylglyoxylic acid, p-methoxyphenylglyoxylic acid, p-ethoxyphenylglyoxylic acid, ethyl p-ethoxyphenylglyoxylate, m-chloro-p-methoxyphenylglyoxylic acid, p-(methylthio)phenylglyoxylic acid, p-(isopropylthio)phenylglyoxylic acid, p-(n-butylthio)phenylglyoxylic acid, p-(ethylthio)phenylglyoxylic acid, sodium (neo-pentylthio)phenylglyoxylate, p-methylphenylglyoxylic acid, or p-chlorophenylglyoxylic acid as the active ingredient were prepared similarly to Example 4, using the said active ingredient in place of p-hydroxyphenylglyoxylic acid, and omitting addition of the sodium chloride.

EXAMPLE 11

Tablets are compounded from the following ingredients:

| | mg./tablet |
|---|---|
| p-hydroxyphenylglyoxylic acid | 500 |

-continued

| | mg./tablet |
|---|---|
| lactose | 30 |
| maize starch | 60 |
| magnesium stearate | 5 |
| | 595 mg. |

The ingredients are thoroughly blended, granulated and then compressed to tablets of the desired size.

EXAMPLE 12

Tablets are compounded from the following ingredients:

| | mg./tablet |
|---|---|
| p-methoxyphenylglyoxylic acid | 500 |
| lactose | 30 |
| maize starch | 60 |
| magnesium stearate | 5 |
| | 595 mg. |

The ingredients are thoroughly blended, granulated and then compressed to tablets of the desired size.

It may be advantageous to coat tablets according to the invention with an enteric coating, e.g. a coating of a material such as cellulose acetate-phthalate or hydroxypropylmethyl cellulose phthalate which does not dissolve in the stomach but dissolves in the intestine, and/or to include in the tablet composition an effervescent material, e.g. sodium bicarbonate and an edible acid such as tartaric acid, in order to avoid de-activation of the active ingredient in the stomach and/or intestine and to enhance the concentration of the active ingredient in the blood.

It may also be desirable to coat tablets with a sugar coating to improve palatability.

Compounds of the formula (I) may be tested for their ability to increase the oxidation of glucose and/or pyruvate by the following tests.

(1) (a) Diaphragm tissue is obtained from rats fed on a high fat diet similar to 'Diet B' described by Zaragoza and Felber (*Horm. Metab. Res.* 1970, 2, 323). Pyruvate oxidation by such tissue is assessed by measurement of the rate of incorporation of carbon-14 carbon-14-labelled pyruvate into carbon dioxide in vitro, as described by Bringolf (*Eur. J. Biochem.* 1972, 26, 360). The rate of pyruvate oxidation is depressed by 50–75% compared with that by diaphragm tissue from rats fed on a normal diet. When the compounds of the formula (I) are added to the medium, they are found to stimulate pyruvate oxidation by diaphragm tissue from fat-fed rats in a dose dependent manner.

The degree of stimulation by the compounds of the formula (I) at a concentration of 2.0 mM (unless otherwise stated) is shown in the following Table.

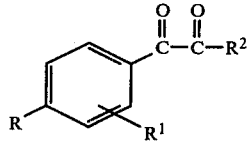

| R | $R^1$ | $R^2$ | % Stimulation |
|---|---|---|---|
| H | H | OH | 25 (at 1mM) |
| OH | H | OH | 104 |
| OH | H | $OC_2H_5$ | 83 |
| $OCH_3$ | H | OH | 127 |
| $OCH_3$ | 3-Cl | OH | 52 |
| $OC_2H_5$ | H | OH | 91 |
| OH | 3-$CH_3$ | OH | 21 |
| OH | 3-I | OH | 55 |
| Cl | H | OH | 71 |
| $CH_3$ | H | OH | 71 |
| $SCH_3$ | H | OH | 123 |
| $SC_2H_5$ | H | OH | 158 |
| S . isopropyl | H | OH | 200 |
| S . n-butyl | H | OH | 113 |
| $SCH_2$ . t-butyl | H | OH | 67 |

(1) (b) The rate of glucose oxidation by isolated hearts from starved rats is measured in a recirculating oxygenated perfusion system, by measuring the rate of incorporation of carbon-14 from carbon-14-labelled glucose into carbon dioxide using a method similar to those described by Morgan et al (*Biochem. J.* 1964, 93, 652). The perfusate contains glucose, palmitate, insulin and bovine serum albumen. The normal rate of glucose oxidation is found to be 1.27±0.32 micromoles/hours (mean of 9 observations).

The ability of compounds of formula (I) to increase the proportion of the active form of the pyruvate dehydrogenase enzyme may be measured by the following test.

(2) Rats fed on a high fat diet as in test (1) (a), are treated either with placebo or with the compound of formula (I), by subcutaneous or intravenous injection or by oral administration, and at various times after treatment the rat hearts are removed and homogenized, under conditions which minimize changes in the proportion of the pyruvate dehydrogenase enzyme which is present in the active form, as described by Whitehouse and Randle (*Biochem. J.* 1973, 134, 651). The total amount of the enzyme present (PDHt) and the amount which is present in the active form (PDHa) are assessed by a method similar to that described by Taylor et al (*J. Biol. Chem.* 1973, 248, 73). The fat-feeding process is found to depress the ratio PDHa/PDHt from a normal value of about 0.7 to a value in the range from 0.05 to 0.2.

The increase in the PDHa/PDHt ratio effected by the compounds of the formula (I) at the stated dose levels is shown in the following Table.

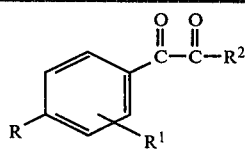

| R | $R^1$ | $R^2$ | Dose (mM/kg) (subcutaneous) | PDHa/PDHt ratio at 1.5 hours Placebo | Compound |
|---|---|---|---|---|---|
| H | H | OH | 1.2 | 0.11 | 0.38 |

-continued

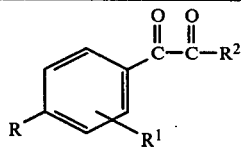

| R | $R^1$ | $R^2$ | Dose (mM/kg) (subcutaneous) | PDHa/PDHt ratio at 1.5 hours Placebo | Compound |
|---|---|---|---|---|---|
| OH | H | OH | 1.2 | 0.16 | 0.28 |
| $OCH_3$ | H | OH | 1.2 | 0.20 | 0.49 |
| $OCH_3$ | 3-Cl | OH | 1.2 | 0.24 | 0.35 |
| $OC_2H_5$ | H | OH | 1.2 | 0.24 | 0.56 |
| $OC_2H_5$ | H | $OC_2H_5$ | 1.2 | 0.24 | 0.35 |
| OH | 3-$CH_3$ | OH | 1.2 | 0.13 | 0.31 |
| $CH_3$ | H | OH | 1.2 | 0.14 | 0.20 |
| $SCH_3$ | H | OH | 1.2 | 0.20 | 0.47 |
|  |  |  | 0.6 | 0.12 | 0.24 |
| $SC_2H_5$ | H | OH | 1.2 | 0.20 | 0.73 |

The ability of compounds of formula (I) to reduce oxygen demand and affect the relative utilization of carbohydrate and lipid metabolites in the heart may be assessed by measuring the effect of the compounds on myocardial blood flow and metabolism in fasted, closed-chest, anesthetized beagle dogs, with cardiac catheterization to enable simultaneous sampling of coronary sinus and arterial blood to be carried out. Coronary sinus blood flow is measured by the hydrogen gas clearance technique described by Aukland et al (*Circulation Res.* 1964, 14, 164). The heart is paced electrically at 155 beats/min. and recordings of hemodynamic parameters (blood pressure, left ventricular pressure and the first derivative of the latter) are made continuously. Control measurements of coronary blood flow are made and samples of blood taken at 40 min. intervals, both in an untreated animal and in the same animal dosed with an infusion of isoprenaline (60 mg/kg/min.), which both stimulates cardiac contraction and increases plasma free fatty acid levels. The compound of formula (I) is then administered intravenously and measurements are made and samples taken again, 40 minutes and 90 minutes later. The blood samples from the artery and coronary sinus are analyzed for oxyhemoglobin, pyruvate and free fatty acid (FFA) content, differences between those of the arterial and coronary sinus blood, when multiplied by coronary blood flow, being a measure of oxygen consumption, pyruvate uptake and FFA uptake by the myocardium respectively.

It is found that p-hydroxyphenylglyoxylic acid at doses of 0.02 to 0.1 millimole/kg. increases myocardial pyruvate uptake both in the presence and absence of isoprenaline, for a period of at least 90 minutes after dosing, in keeping with its primary action as a PDH stimulator. Myocardial blood flow is also increased and myocardial oxygen consumption is decreased both in the presence and absence of isoprenaline.

The ability of compounds of formula (I) to decrease blood glucose levels may be assessed by measuring their effect on blood glucose levels in rats in which diabetes has been induced by treatment with streptozotocin (85 mg./kg.). Four days after such treatment, a number of rats are given 1 millimole/kg. of the compound by intraperitoneal injection and a similar number are given placebo. The doses are repeated after a further 24 hours and 48 hours. Blood samples are taken from a tail vein immediately before each dosage (which is 2 hours after removal of the animals from food) and 1, 2 and 3 hours after the third dose. After 2 days of treatment with p-hydroxyphenylglyoxylic acid (i.e. immediately before the third dose with 1 millimole/kg.), blood glucose levels have been found to have declined from 376±6 mg./100 ml. to 358±9 mg./100 ml., compared with a slight increase from 373±8 mg./100 ml. to 383±10 mg./100 ml. for animals treated with placebo; while 3 hours after the third dose the blood levels had declined still further, to 344±9 mg./100 ml., compared with a value of 369±9 mg./100 ml. for animals treated with placebo (all figures are averages for 8 animals).

What is claimed is:

1. A method for treating diabetes in a human subject having such condition which comprises orally or parenterally administering to said human subject a diabetes treating amount of a compound selected from the group consisting of a compound of the formula

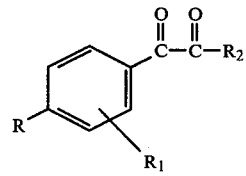

wherein R is selected from the group consisting of hydrogen, alkyl having from one to four carbon atoms, hydroxy, alkoxy having from one to four carbon atoms, alkylthio having from one to five carbon atoms, alkanoyloxy having from two to four carbon atoms, chloro, fluoro, bromo and iodo; $R_1$ is selected from the group consisting of hydrogen, alkyl having from one to four carbon atoms, chloro, bromo, fluoro and iodo; $R_2$ is selected from the group consisting of hydroxy and alkoxy having from one to four carbon atoms; and a pharmaceutically acceptable base salt wherein $R_2$ is hydroxy.

2. A method of claim 1 wherein $R_1$ is hydrogen and $R_2$ is hydroxy.

3. The method of claim 2 wherein R is hydroxy.

* * * * *